United States Patent [19]

Woodhead et al.

[11] Patent Number: 4,761,382
[45] Date of Patent: Aug. 2, 1988

[54] IMMUNOLOGICAL PROCEDURE FOR DETECTING OR QUANTIFYING SUBSTANCES

[75] Inventors: James S. Woodhead, Gwent; Ian Weeks, Cardiff, both of United Kingdom

[73] Assignee: The Welsh National School of Medicine, Cardiff, United Kingdom

[21] Appl. No.: 13,215

[22] Filed: Feb. 5, 1987

Related U.S. Application Data

[63] Continuation of Ser. No. 529,751, Sep. 6, 1983, abandoned.

[30] Foreign Application Priority Data

Sep. 10, 1982 [GB] United Kingdom ................. 8225933

[51] Int. Cl.⁴ ................. G01N 33/536; G01N 33/542
[52] U.S. Cl. ....................................... 436/536; 435/7; 435/8; 436/500; 436/537; 436/800; 436/805
[58] Field of Search ............... 435/7, 8; 436/500, 536, 436/537, 800, 805

[56] References Cited

U.S. PATENT DOCUMENTS 4,276,051 6/1981 Ginsberg et al. ..................... 422/64

Primary Examiner—Christine M. Nucker
Attorney, Agent, or Firm—Young & Thompson

[57] ABSTRACT

This invention relates to a method of detecting, analyzing, quantifying, or locating a substance of biological interest by an immunoassay in which a first component of an immune reaction in the form of an antigen, hapten, or antibody, is linked with one or more components of a chemiluminescent reaction, and the other component of the immune reaction, the analyte, is complexed therewith to cause entropic and/or ethalpic changes in a subsequent light emitting action as compared with the reaction of uncomplexed labelled component, the reaction being observed and compared to provide information on the immune complex formation. Preferably the intensity of light emission of the rate of photonic emission or the rate of change of intensity of emission are observed compared with the equivalent properties of the uncomplexed component.

1 Claim, 2 Drawing Sheets

GRAPHICAL REPRESENTATION OF CHEMILUMINESCENT REACTION RATE AS A FUNCTION OF TIME AND AFP CONCENTRATION IN HOMOGENEOUS LABELLED ANTIBODY IMMUNOASSAY

DOSE-RESPONSE CURVE OF HOMOGENENEOUS LABELLED ANTIBODY AFP ASSAY (EXAMPLE 1).

IMMUNOLOGICAL PROCEDURE FOR DETECTING OR QUANTIFYING SUBSTANCES

This application is a continuation of application Ser. No. 529,751, filed 9/6/83, abandoned.

This invention relates to methods designed for use in the analysis, assay or localisation of proteins, polypeptides, haptens and other substances of biological interest. The invention utilises immune complex formation as a measure of the amount of analyte present by means of the use of antigens, haptens or antibodies labelled with chemiluminescent molecules. In the past such biological molecules have been labelled using radioactive isotopes which suffer problems of instability, insensitivity, inconvenient quantification and disposal. In contrast chemiluminescent labels are non hazardous, stable and can be detected with high sensitivity using simple photon counting equipment. In the context of this invention the term chemiluminescence is used to distinguish this phenomenon from other forms of luminescence, e.g. fluorescence, phosphorescence, etc., and is taken to include the related phenomenon of bioluminescence. In a further aspect of the invention the concentration of immune complexes, and hence of the analyte, is determined by changes in certain physiocochemical parameters of the chemiluminescent reaction of such labelled species upon formation of immune complexes.

In some preferred forms of the invention these changes are involved with the rate of the chemiluminescent reaction, notably the formation of the excited states. It is a particular and important feature of the invention that quantitation of the analyte concentration does not require prior separation of analyte-bound and unbound labelled immunoreactant.

Many chemical species are capable of chemiluminescence, which is the phenomenon observed when the vibronically excited product of an exergonic reaction reverts to its ground state with photonic emission. Such reactions are usually of an oxidative nature and may or may not involve a catalytic component. For example Luminol requires the presence of a catalyst for the chemiluminescent reaction, whereas acridinium esters do not require a catalyst. Broadly stated, a chemiluminescent reaction consists of two stages, these being the formation of excited states as represented generally by the equation

$$A + B \rightarrow C$$

and the subsequent decay thereof to the unexcited "ground" states represented generally by the equation

$$C \rightarrow D.$$

For any given excited state which yields a corresponding ground state arising from energy loss by photonic emission, the rate of decay is proportional to the concentration of molecules in the excited states. The decay rate coefficient of such a reaction, which acts to equate the aforementioned proportionality is thus first order and exponentially relates the concentration of the excited states to a particular increment of time which constitutes part of the total lifetime of the reaction.

By comparison the rate of formation of excited states is an inherently more complex relationship than is the simple decay of excited states. The rate of formation is a function of the excited state precursor concentration (i.e. the concentration of the molecular luminescent label before being excited) and also of the concentration of the other reactants in the system. The excitation rate coefficient in this instance is a compound of a number of kinetic and thermodynamic parameters pertaining to the reactions which are involved in the formation of the excited states. Thus a change in such parameters such as may be experienced by prior chemical or physical interactions of the chemiluminescent molecule may be reflected as a change in excited state formation rate. Further, such a change will also be reflected by the relationship between the number of photons emitted or the rate at which they are emitted and an increment of time over which the reaction is taking place. There are unique advantages to be gained from utilizing the excitation phase to quantify a chemiluminescent reaction. Firstly, it is extremely rapid—accurate measurements can be made within 1 second or less. Secondly, because of the short time scale there is a low background which increases the sensitivity of detection, and thirdly the use of a rate measurement reduces interference due to inner filter effects.

Broadly stated the invention consists in a method of detecting, analysing, quantifying, or locating a substance of biological interest by an immunoassay in which a first component of an immune reaction in the form of an antigen, hapten, or antibody, is linked with one or more components of a chemiluminescent reaction, and the other component of the immune reaction, the analyte, is complexed therewith to cause entropic and/or ethalpic changes in a subsequent light emitting action as compared with the reaction of uncomplexed labelled component, the reaction being observed and compared to provide information on the immune complex formation. Preferably the intensity of light emission or the rate of photonic emission or the rate of change of intensity of emission are observed compared with the equivalent properties of the uncomplexed component. Preferably, a graphical representation is firstly obtained of the function relating either the intensity or the rate of photonic emission (and hence the excited state concentration) to the reaction time following initiation of the light-emitting reaction of the labelled immunoreactant. A graph is also prepared for labelled immunogen which has previously been incubated with the corresponding analyte of interest. Changes in the slope of the relationships at any given point corresponding to one of the variables of the functions are a measure of the analyte concentration and can be compared with those of a series of known analyte concentrations. If the labelled immunoreactant is a labelled antigen or hapten and is used in a competitive binding system, the kinetic and thermodynamic parameters of the unbound labelled immunoreactant are compared with those of labelled immunoreactant previously incubated with analyte and antibody or binding protein. The changes in kinetic and thermodynamic parameters which result in changes in the rate of photon emission will be inversely proportional to the concentration of analyte. If the labelled immunoreactant is a labelled antibody, this may be used in a analogous competitive system for the measurement of antibodies in biological fluids such as serum. In a preferred aspect of the invention the labelled antibodies would be used in molar excess over the analyte present. The excess could be 500% but would preferably be no more than 100%, more preferably no more than 20%. In a further aspect of the invention the kinetic changes observed are amplified by increasing the size of the immune complexes formed by the use of immobilized antibody. In this situation the change in the rate of excitation is enhanced when the size of the antigen antibody complex is enlarged by the presence of polymerized antibody or antibody linked to a solid support such as cellulose.

Preferably, the quantity of analyte is reflected by a change in the graphical representation of the function relating excited state concentration (or the rate of change of excited state concentration or further derivation thereof) to the reaction time. These parameters are a function of the photonic emission of the chemiluminescent label which is quantified using photon counting apparatus. Several prarmeters of the function or its derivatives may be monitored so as to provide a measure of analyte concentration, for example the slope of the function at any given point on the reaction profile, the amplitude at any point, the integration of any part of the reaction profile, or the time taken to reach a peak or a preselected value, or any combination of several properties.

Preferably the chemiluminescent labels are acridinium salts, luminol, dioxetanes, bis-oxalates, fluorescein, pyrogallol, lucigenin, lophine, photoproteins, or derivatives of these compounds which can be associated with antigens, antibodies and haptens so as to provide chemiluminescent immunoreactants.

In contrast to existing homogeneous immunoassay techniques using enzyme or fluorescent labels, this invention is not restricted to the measurement of small molecules or haptens but may be applied to the quantitation of all antigenic compounds including drugs (e.g. barbiturates, salicylates, phenytoin, morphine, heroin, methotrexate, digoxin), steroids (e.g. testosterone, progesterone, oestradiol, oestriol, cortisol, aldosterone, vitamin D), cyclic nucletides, thyroxine, triiodothyronine or proteins (e.g. insulin, growth hormone, parathyroid hormone, thyroid stimulating hormone, prolactin, adrenocortotrophic hormone, alphafetoprotein, ferritin, human immunoglobulin (Ig) rabbit IgG, mouse IgG, guinea pig IgG, sheep IgG, interferon, components of the complement system and bacterial and viral antigens).

Thus it will be seen that the invention provides a method for the detection or quantitation of substances of biological interest by a homogeneous immunoassay procedure in which antigens, antibodies or haptens are labelled with chemiluminescent molecules, the physicochemical properties of which are modified in a measurable dependent way upon immune complex formation.

In the context of the invention a homogeneous assay may be defined as one in which the properties of the label are changed in a dose-dependent or concentration-dependent way on formation of the immune complex, thus avoiding the need for separation of the bound and free analyte fractions.

The invention may be performed in various different ways and a number of examples will now be dscribed in detail by way of illustration.

EXAMPLES

1. Homogeneous assay of human$\alpha_1$-fetoprotein (AFP) using labelled antibodies.

A series of solutions of AFP standard in sera are made and a known volume, preferably 50 $\mu$l, and hence a known quantity of AFP is placed in a series of assay tubes. Identical volumes of unknown sera to be investigated are placed in another series of assay tubes and 0.1M phosphate buffer, pH6.3 (100 $\mu$l) placed in all tubes. Antibodies to AFP (polyclonal or monoclonal), labelled with acridinium ester and preferably having a specific activity of $2 \times 10^5$ luminescent counts per nanogram are added to each tube such that they are present in excess of AFP analyte. The tubes are incubated at room temperature preferably for 30 mins, each tube is placed sequentially in a luminometer and the photons emitted upon initiation of the chemiluminescent reaction counted for 5 seconds or less. The rate of analysis of the tubes is adjusted so as to match the rate of addition of reagents prior to incubation. The chemiluminescent reaction is initiated by injection preferably of 200 $\mu$l of an aqueous solution containing 0.5M sodium hydroxide and 0.1% (V/V) of "100 volume" (i.e. 30% weight/volume) hydrogen peroxide. The rate of formation of excited states (i.e. the rate of photon emission over a suitable time period) is measured for standards and unknowns using photon counting equipment. This may be done in several different ways. In one process the total number of photons emitted over a one second time period is recorded, and in another process the relationship which expresses the rate of photonic emission as a function of time is differentiated to enable calculation of the initial rate of reaction. In either case the results corresponding to the samples having unknown analyte concentrations are compared with those obtained from a series of standards of known amounts of analyte by constructing a calibration curve from the latter examples of which are given in FIGS. 3 and 4.

Figure 1:
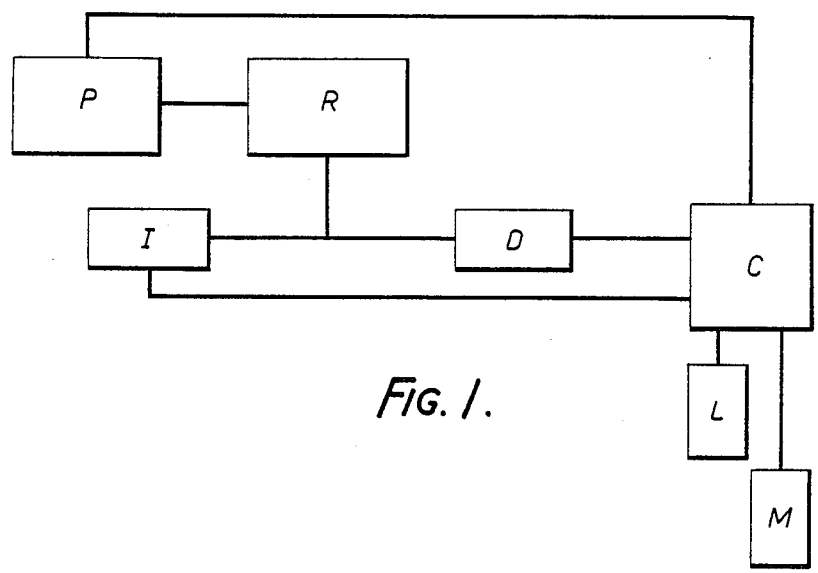
Figure 2:
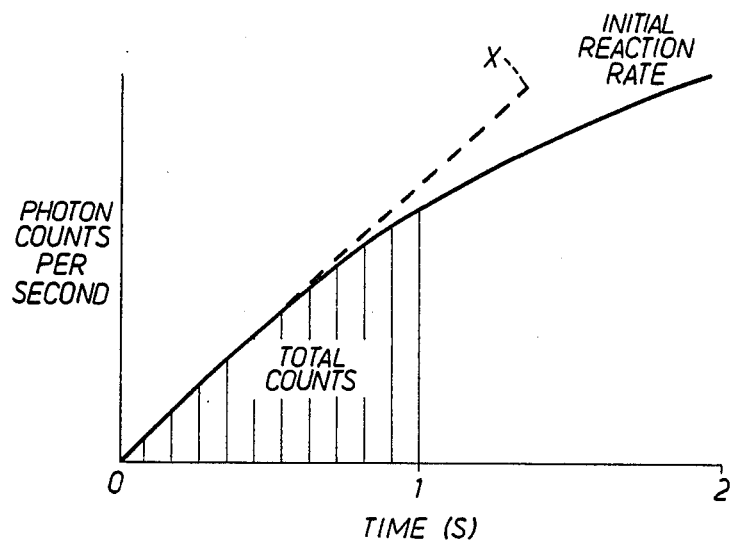
Figure 3:
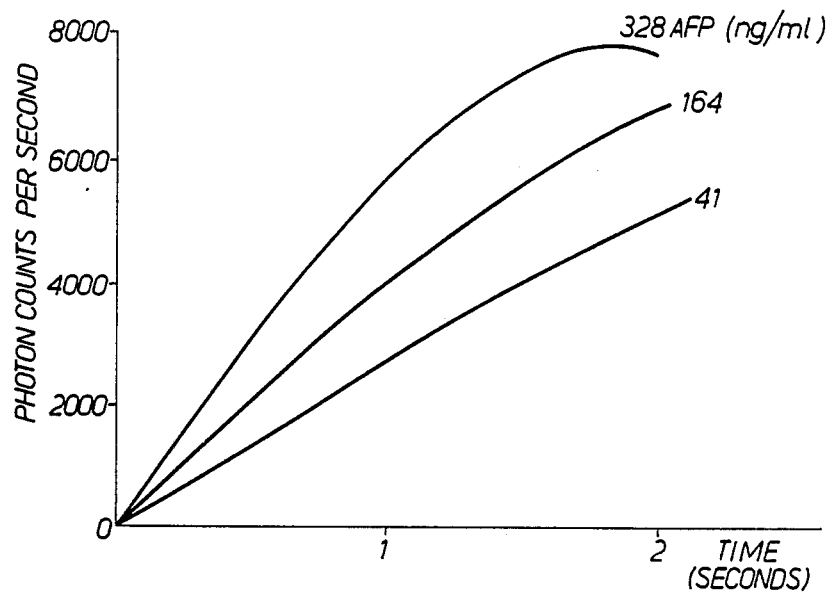
FIG. 3 is a graphical representation of chemiluminescent reaction rate as a function of time and AFP concentration in homogeneous labelled antibody immunoassay. The three curves represent three different AFP concentrations, at 328, 164 and 41 ng/ml.
Figure 4:
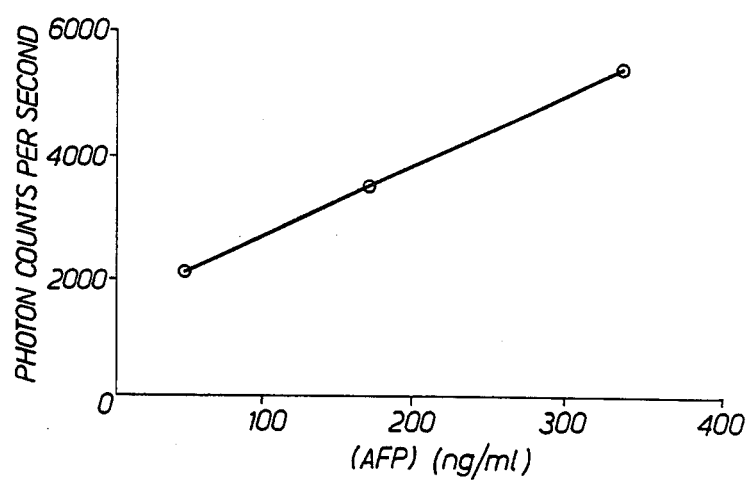
FIG. 4 is a defined dose-response curve showing how the count rate varies linearly with the concentration.

A typical apparatus is illustrated diagrammatically in FIG. 1 where P is a photon counter, R is a data reduction unit, I is an integrator, D is a differentiator, C is a computer, L is a printer, M is a disk drive. FIG. 2 illustrates a typicalgraph illustrating photon count per second plotted against time, and illustrating the way in which the actual emission rate varies, (the amplitude at any point on the curve) and also the rate of change (the slope of the curve at any point) and the overall count (the integrated area under the curve). In FIG. 2 the line X indicates the slope of the initial reaction rate. It will be seen that other characteristics can be derived or deduced therefrom such as the "time to peak", or the total count up to 0.5 secs. or any other selected interval.

2. Homogeneous assay of human$\alpha_1$-fetoprotein (AFP) using labelled antigens.

Standard and unknown sera (50 $\mu$l) are incubated with the purified AFP labelled with acridinium ester molecules to a specific activity of $2 \times 10^5$ luminescent counts per nonogram and with polyclonal or monoclonal anti AFP antibodies at a concentration which is known to bind 50% of the labelled AFP after four hours at room temperature. The tubes are incubated at a final assay volume of 200 $\mu$l (0.1M phosphate buffer, 0.15M sodium chloride pH6.3) for four hours at room temperature. The mixtures are then measured luminometrically by injection of alkaline hydrogen peroxide as before. The rate of excited state formation observed for the samples is compared with that of the standards and the AFP content quantified by interpolating as in Example 1.

3. Homogeneous Assay of Triiodothyronine (T3).

Standards and unknown samples (50 μl) containing $T_3$ are diluted to 100 μl with HEPES buffer (0.01M, pH 7.4) containing 0.25% merthiolate. Fifty μl $T_3$ labelled with acridinium ester are added followed by 50 μl antibody to $T_3$. After 30 minutes reaction the luminescence is measured as described in example 2 following injection of alkaline hydrogen peroxide. The rate of excited state formation observed in the samples is compared with that of standards and the $T_3$ content quantified by interpolation as in example 1.

4. Homogeneous Assay of Free $T_3$.

This assay is based on the principle that $T_3$ with acridinium ester linked through the amino group will not react with naturally occurring binding proteins (e.g. thyroxine binding globulin) but binds to antibody. The assay for free $T_3$ is carried out as follows. Standards or unknown samples containing $T_3$ (50 μl) are diluted to 100 μl with HEPES buffer (0.01M, pH 7.4). 50 μl labelled $T_3$ are added followed by 50 μl antibody solution. During a 30 minute reaction label is bound to antibody. This binding in inhibited by free $T_3$ which competes for antibody binding sites. After the reaction period, therefore, luminescence is meaured following addition of alkaline hydrogen peroxide in the manner described. The rate of excited state formation in samples is compared with that of standards and the free $T_3$ concentration quantified by interpolation as in example 1.

5. Homogeneous assay of insulin.

Standard and unknown sera (50 μl) are incubated with purified insulin labelled with acridinium ester molecules and with pre-precipitated insulin antibodies. These represent high molecular weight complexes for enhanced change of rate of the chemiluminescent reaction as described above. The mixture is incubated for 3 hours at room temperature, in 200 μl 0.01M phosphate buffer (pH6.3) and the tubes analysed luminometrically. The reaction rates observed for the unknown samples are compared with those of the standards and hence the insulin concentrations determined by interpolation.

6. Homogeneous assay of serum thyroid stimulating immunoglobulins.

A solublised thyroid membrane preparation in PBS (pH6.3) containing 0.1% HSA is incubated with 100 μl of serum IgG fraction to be investigated. The amount of membrane being sufficient to bind 10-30% of the labelled thyrotrophin (TSH) being used.

Following incubation at room temperature for 1 hour, acridinium ester labelled TSH is added and the mixture incubated for an additional 1 hour period. The assay tubes are measured luminometrically as in example 1 and the rate of emission compared with that of a normal serum IgG preparation to establish the presence or absence of pathologically significant amounts of thyroid stimulating antibodies.

We claim:

1. In a method of quantifying a substance of biological interest by a homogeneous immunoassay, in which a first component of an immune reaction in the form of an antigen, hapten, or antibody, is linked with one or more components of a chemiluminescent reaction, and the corresponding component of the immune reaction is complexed therewith to cause entropic and/or enthalpic changes in a subsequent light emitting reaction characterized by the formation of an electronically excited state and the simultaneous decay of said electronically excited state according to the respective equations $$A + B \rightarrow C$$

$$C \rightarrow D;$$

the improvement comprising measuring the rate of change of the intensity of light emission of the light emitting reaction from the said complexed labelled component, only during the period when the intensity of emission therefrom is rising, thereby to determine said rate of change only when said formation of an electronically excited state predominates over the decay thereof, reacting the uncomplexed labelled component with its corresponding component in the immune reaction, measuring the rate of change of the intensity of light emission of the light emitting reaction of the uncomplexed labelled component only during the period when the intensity of emission therefrom is rising, thereby to determine the latter said rate of change only when said formation of an electronically excited state predominates over the decay thereof, and mathematically processing and comparing the said measurements to quantify the substance of interest.

* * * * *

UNITED STATES PATENT AND TRADEMARK OFFICE
CERTIFICATE OF CORRECTION

PATENT NO. : 4,761,382

DATED : August 2, 1988

INVENTOR(S) : James S. Woodhead et al.

It is certified that error appears in the above-identified patent and that said Letters Patent is hereby corrected as shown below:

On the title page Item [75] insert -- Anthony K. Campbell, Whitchurch, United Kingdom --, as a joint inventor.

Signed and Sealed this

Seventeenth Day of January, 1989

Attest:

DONALD J. QUIGG

Attesting Officer

Commissioner of Patents and Trademarks